United States Patent [19]

Uchida et al.

[11] Patent Number: 5,051,347

[45] Date of Patent: Sep. 24, 1991

[54] SILVER HALIDE PHOTOGRAPHIC LIGHT-SENSITIVE MATERIAL CONTAINING A NOVEL CYAN COUPLER

[75] Inventors: Takashi Uchida; Toyoaki Masukawa; Noritaka Nakayama, all of Hino, Japan

[73] Assignee: Konica Corporation, Tokyo, Japan

[21] Appl. No.: 549,273

[22] Filed: Jul. 6, 1990

[30] Foreign Application Priority Data

Jul. 17, 1989 [JP] Japan .................................. 1-182568

[51] Int. Cl.$^5$ .............................................. G03C 7/38
[52] U.S. Cl. .................................. 430/558; 430/384; 430/385
[58] Field of Search ........................ 430/558, 384, 385

[56] References Cited

U.S. PATENT DOCUMENTS 4,921,783  5/1990  Nakayama et al. .................. 430/558

FOREIGN PATENT DOCUMENTS 0320778  6/1989  European Pat. Off. .

Primary Examiner—Charles L. Bowers, Jr.
Assistant Examiner—Lee C. Wright
Attorney, Agent, or Firm—Frishauf, Holtz, Goodman & Woodward

[57] ABSTRACT

A silver halide photographic light-sensitive material containing a novel cyan coupler is disclosed. The cyan coupler is represented by the following Formula I:

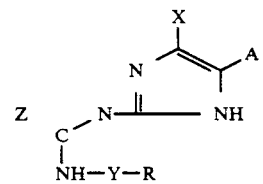

wherein A represents an organic group; X represents a hydrogen atom or a group capable of splitting off upon a reaction with an oxidation product of a color developing agent; Z represents the group of atoms capable of forming a five or six-membered heterocyclic ring together with carbon and nitrogen atoms; Y represents a linkage group; and R represents a hydrogen atom or an organic group.

19 Claims, No Drawings

SILVER HALIDE PHOTOGRAPHIC LIGHT-SENSITIVE MATERIAL CONTAINING A NOVEL CYAN COUPLER

FIELD OF THE INVENTION

The present invention relates to a silver halide color photographic light-sensitive material containing a novel cyan coupler.

BACKGROUND OF THE INVENTION

Generally, in a silver halide color photographic light-sensitive material, a color developing agent oxidized by an exposed silver halide reacts with a dye-forming coupler to form a dye.

The formed dye is strongly demanded to have a sharp absorption spectrum for good color reproduction.

Phenol compounds or naphthol compounds have conventionally been used as cyan couplers.

These compounds are described in U.S. Pat. Nos. 2,369,929 and 2,474,293. The absorption spectrums of cyan dye images obtained from these phenol and naphthol compounds are not so sharp in a shorter wavelength region.

Japanese Patent publication Open to Public Inspection (hereinafter referred to as Japanese Patent O.P.I. Publication) Nos. 226653/1988 and 158441/1989 disclose imidazole couplers, which are described as having good spectral absorption characteristics. However, dye images obtained from these couplers have serious problems in light fastness and color recoverability when processed in a repeatedly used bleacher or a bleach-fixer.

SUMMARY OF THE INVENTION

It is the first object of the invention to provide a silver halide photographic light-sensitive material containing a novel cyan coupler capable of forming a cyan dye having an excellent spectral absorption characteristic and an improved light fastness.

It is the second object of the invention to provide a silver halide photographic light-sensitive material containing a novel cyan coupler having an excellent color recoverability.

The above objects of the invention are accomplished by a silver halide photographic light-sensitive material comprising a support having thereon the photographic component layers including at least one silver halide light-sensitive emulsion layer containing silver halide grains and a cyan coupler represented by the following Formula I:

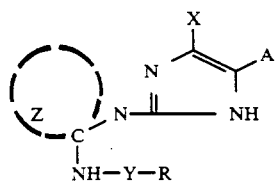

wherein A represents an organic group; X represents a hydrogen atom or a group capable of splitting off upon a reaction with an oxidation product of a color developing agent; Z represents the group of atoms capable of forming a 5- or 6-member heterocyclic group together with carbon and nitrogen atoms; Y reprents a linkage group; and R reprents a hydrogen atom or an organic group.

DETAILED DESCRIPTION OF THE INVENTION

In Formula I, the organic group represented by A is an alkyl group, an aryl group, a heterocyclic group, —NHCOR', —NHSO$_2$R', —NHCONHR', —NHCOOR', or —Y'R", wherein R' represents a hydrogen atom, an alkyl group or an aryl group; R" represents an alkyl, aryl or heterocyclic group; and Y' represents an oxygen, nitrogen or sulfur atom.

A is preferably an aryl or heterocyclic group. The aryl group is preferably a phenyl or naphthyl group. The heterocyclic group is preferably a thienyl, furyl, pyrrolyl, pyrazolyl, pyridyl or isooxazolyl group.

A is more preferably a phenyl group which has in an ortho-position a group capable of forming a hydrogen bond, such as amide, sulfonamide, carbamoyl and sulfamoyl groups.

The group represented by X and capable of splitting off upon a reaction with an oxidation product of a color developing agent, is a halogen atom, a hydroxyl group, an alkoxy group, an aryloxy group, a heterocyclicoxy group, an acyloxy group, a sulfonyloxy group, an alkoxycarbonyloxy group, an aryloxycarbonyl group, an alkyloxalyloxy group, an alkoxyoxalyloxy group, an alkylthio group, a mercapto group, an arylthio group, a heterocyclicthio group, an alkoxythiocarbonylthio group, an acylamino group, a substituted amino group, a nitrongen-containing heterocyclic group having a bonding site on N, a sulfonamide group, an alkyloxycarbonylamino group, an aryloxycarbonylamino group, or a carboxyl group. It is preferably a halogen atom, particularly a chlorine atom.

The 5- or 6-member heterocyclic group represented by

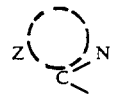

is a pyrrolyl, imidazolyl, pyrazolyl, pyrrolidinyl, imidazodinyl, pyrazolidinyl, piperazinyl, morpholinyl, or thiazolidinyl group.

These heterocyclic groups may have a substituent other than —NH—Y—R. Y is a mere bond or a divalent linkage group such as —CO—, —COO—, —SO$_2$—and —CONH—. R is a hydrogen atom or an organic group such as an alkyl group, an aryl group and a heterocyclic group, which may have a substituent.

The following are typical examples of the cyan coupler of the invention.

| No. | X | A | B |
|---|---|---|---|
| 1 | —Cl | 2-methylphenyl-NHCOCH(C₃H₇(i))O-(2,4-di-C₅H₁₁(t))phenyl | 1-methyl-3-phenyl-4-chloro-5-(NHCO-phenyl)pyrazole |
| 2 | —Cl | 2-methylphenyl-NHCOCH(C₃H₇(i))O-(2,4-di-C₅H₁₁(t))phenyl | 1-methyl-3-phenyl-4-chloro-5-(NHCOCH₃)pyrazole |
| 3 | —SCH₂CH₂COOH | 2-methyl-4-methoxyphenyl-NHCOCH(C₄H₉)O-(2,4-di-C₅H₁₁(t))phenyl | 1-methyl-3-methyl-5-(NHCOOC₂H₅)pyrazole |
| 4 | —SCH₂CH₂COOH | 3,5-dichloro-2-methylphenyl (NHCOOC₁₅H₃₁) | 1-methyl-3-C₄H₉(t)-5-(NHSO₂-phenyl)pyrazole |
| 5 | —Cl | 2-methylphenyl-NHCOCH(C₃H₇(i))O-(2,4-di-C₅H₁₁(t))phenyl | 1-methyl-3-C₄H₉(t)-5-(NHCO-pentafluorophenyl)pyrazole |
| 6 | —Cl | 2-methylphenyl-NHSO₂-(2-OC₈H₁₇,5-C₈H₁₇(t))phenyl | 1-pyrrolidinyl-2-(NHCOC₃H₇) |
| 7 | —Cl | 4-chloro-2-methylphenyl-NHSO₂-(4-OC₁₂H₂₅)phenyl | 4,5-dichloro-2-(NHCOOCH₃)imidazole |

-continued

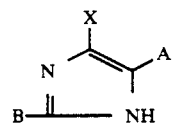

| No. | X | A | B |
|---|---|---|---|
| 8 | —Cl | (2-methyl-4-(benzamido)phenyl)-NHCOCH(C6H13)-O-(2,4-di-tert-butylphenyl) | morpholino with NHSO2N(CH3)2 |
| 9 | —Cl | 2-methylphenyl-NHCOOC2H5 | 1-methyl-3-phenyl-4-chloro-5-[NHCOCH(C3H7(i))-O-(2,4-di-tert-pentylphenyl)]pyrazole |
| 10 | —Cl | 2-methylphenyl-NHCOOC12H25 | 1-methyl-4-methyl-5-anilino-3-(NHCOCF3)pyrazole |
| 11 | —Cl | —C8H17(t) | 1,3-dimethyl-4-phenyl-5-(NHCONHC6H5)pyrazole |
| 12 | —H | 2-methylphenyl-NHCOCH(C3H7(i))-O-(2,4-di-tert-pentylphenyl) | 1-methyl-3-tert-butyl-5-amino-pyrazole |
| 13 | —Cl | 2-methylphenyl-NHCO(CH2)2OCOCH2-O-(4-chloro-2-octylphenyl) | piperazine with NHCOCH3 substituents and N—COCH3 |

-continued
| No. | X | A | B |
|---|---|---|---|
| 14 | —Cl | 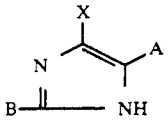 |  |
| 15 | 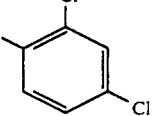 | 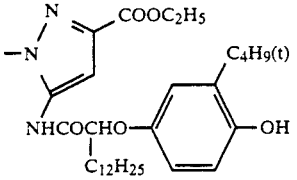 | 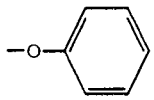 |
| 16 | 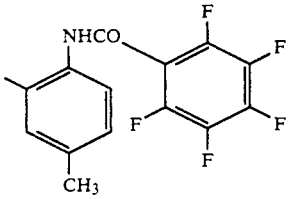 | 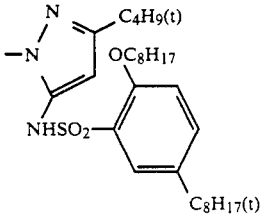 | 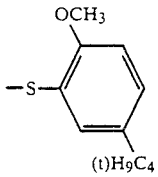 |
| 17 | —Cl | 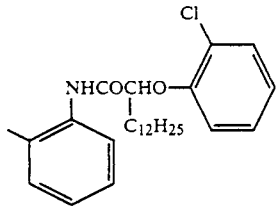 | 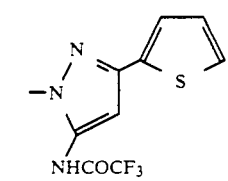 |
| 18 | —Cl | 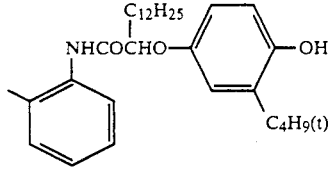 | 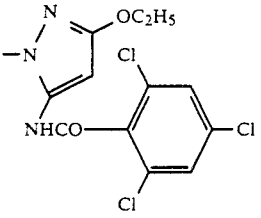 |
| 19 | —Cl | 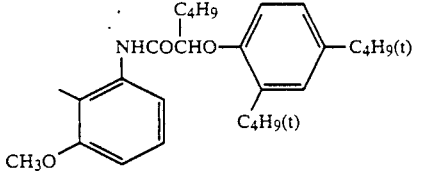 | 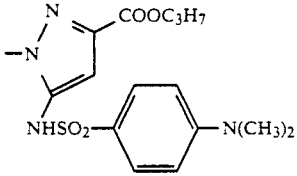 |
| 20 | —Cl | 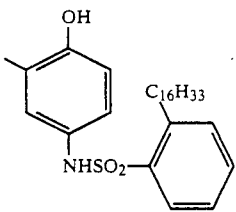 | 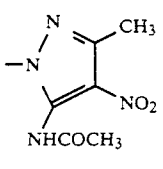 |

-continued
|     |     |     |     |
| --- | --- | --- | --- |
| No. | X | A | B |
| 21 | —Cl | 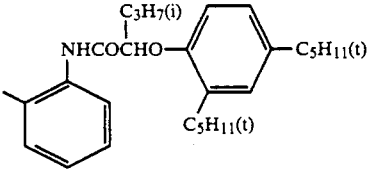 | 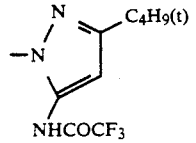 |
| 22 | —Cl | 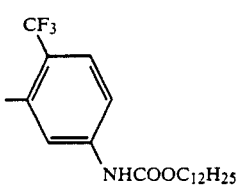 | 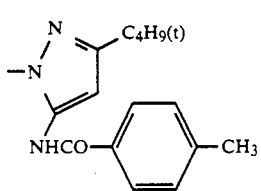 |
| 23 | —Cl | 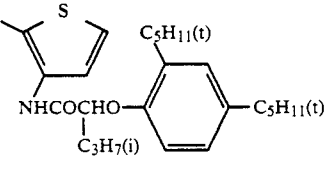 | 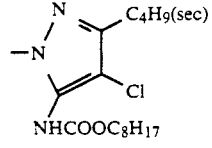 |
| 24 | —Cl | 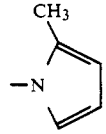 | 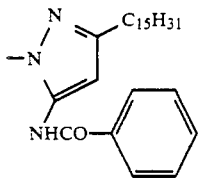 |
| 25 | —Cl | 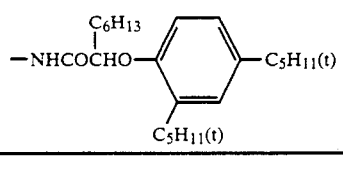 | 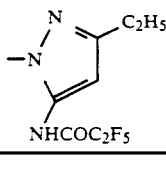 |
The following are synthesis examples of the cyan coupler of the invention:
Synthesis of Coupler 1
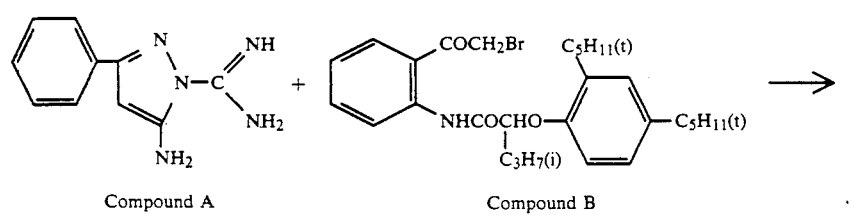
Compound A    Compound B

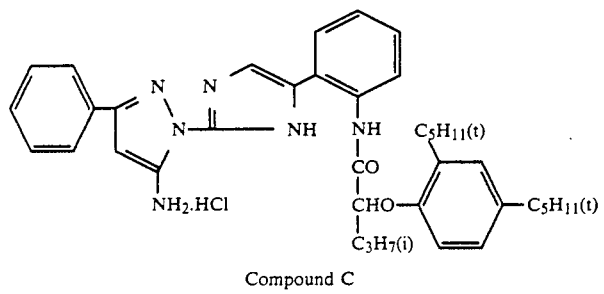

Compound C

Compound A 22.5 g and Compound B 19.7 g dissolved in 100 ml of dimethylformamide were left reacting for 5 hours at a room temperature. The reaction solution was poured into water, and the oily product was extracted with ethyl acetate. The ethyl acetate layer was washed sufficiently with dilute hydrochloric acid and water, and then dried with magnesium sulfate, followed by distilling off the solvent. The oily residue was subjected to B.O. treatment with a hexane-ethyl acetate (9:1) spreading solvent, whereby 18.5 g of Compound C were obtained.

2.

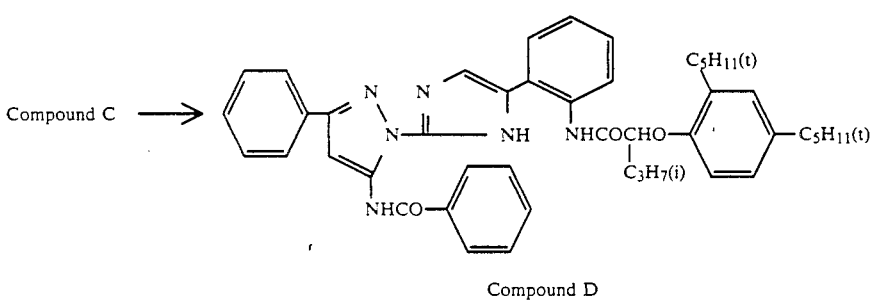

Compound D

To a solution of Compound C 18.0 g dissolved in 240 ml of acetonitrile were added 4.4 g of benzoyl chloride and 5.0 g of pyridine, and the solution was heated for refluxing for 3 hours. Then, it was cooled and the deposited crystals were filtered and recrystallized in acetonitrile, whereby Compound D 18.0 g of white crystals were obtained.

3. Compound D→Coupler 1

To a solution of Compound D 15 g dissolved in 150 ml of dimethylformamide were added 5.4 g of N— chlorosuccinic acid imide, and the solution was allowed to stand over a whole day at a room temperature. The reaction solution was poured into water and extracted with ethyl acetate, followed by washing with water and drying with magnesium sulfate. The crystals obtained after distilling off the solvent were recrystallized in acetonitrile, whereby 12.5 g of Coupler 1 were obtained.

The chemical structures of Compound C, Compound D and Coupler 1 were identified with NMR and a mass spectrum.

The coupler of the invention is used normally in an amount of $2 \times 10^{-3}$ to $8 \times 10^{-1}$ mole, and preferably $1 \times 10^{-2}$ to $5 \times 10^{-1}$ mole per mole of silver halide.

It may be used in combination of two or more and with the other cyan couplers.

It may be incorporated into a light-sensitive material in accordance with various methods such as solid dispersion, latex dispersion and oil-in-water emulsification dispersion.

The oil-in-water emulsification dispersion method can be used for addition of the coupler of the invention, in which the coupler is dissolved in a high-boiling solvent having a boiling point of more than 150° C. such as tricresyl phosphate and dibutyl phthalate, if necessary, together with a low-boiling organic solvent such as ethyl acetate and butyl propionate; the solution is emulsified and dispersed in a hydrophilic binder such as an aqueous gelatin solution with a surface active agent; and then the dispersion is added to a coating solution.

The silver halide photographic light-sensitive material of the invention can be applied to a color negative film, a color positive film, a color reversal film or a color photographic paper. It is applied particularly preferably to the color photographic paper.

The light-sensitive material of the invention applied to the color photographic paper, in which color is reproduced by subtraction, usually comprises a support having thereon the photographic component layers including the light-sensitive silver halide emulsion layers such as the green-sensitive, red-sensitive and blue-sensitive emulsion layers containing the magenta, cyan and yellow couplers, respectively, and non-light-sensitive layers.

Silver halides used in the invention may be conventional ones such as silver bromide, silver iodobromide, silver iodochloride, silver chlorobromide and silver chloride.

The silver halide emulsion may be chemically sensitized by sulfur sensitization, selenium sensitization, reduction sensitization or noble-metal sensitization, and may also be spectrally sensitized to prescribed wavelength regions with sensitizing dyes.

In the invention there may be used conventional additives such as an antistain agent, a hardener, a plasticizer, a polymer latex, a UV absorber, a formalin scavenger, a mordant, a development accelerator, a development retarder, a brightening agent, a matting agent, a lubricant, an antistatic agent, a surfactant, and an image stabilizer.

The light-sensitive material of the invention may be subjected to conventional processings such as color developing, bleaching, fixing or bleach-fixing, stabilizing, and washing.

EXAMPLES

The present invention is explained hereunder by referring to the examples.

EXAMPLE 1

Each of the couplers given in Table 1 was dissolved in ½ part by weight of dioctyl phthalate and 3 parts by weight of ethyl acetate, and the solution was emulsified and dispersed in a 5% gelatin solution containing Alkanol XC (product of DuPont) as a surfactant. The dispersion was mixed with a silver chlorobromide emulsion containing 80 mole% silver bromide in a coupler content of 0.35 mole per mole of silver, and the liquid was coated and dried on a paper support laminated on both sides with polyethylene, whereby Samples 1 to 12 were prepared. (Coated amount of coupler: $1.2 \times 10^{-7}$ mole/cm$^2$, coated weight of silver: $3.7 \times 10^{-2}$ mg/cm$^2$, coated weight of gelatin: $1.6 \times 10^{-1}$ mg/cm$^2$)

The above samples were exposed through an optical wedge in a usual manner, and then processed in the following steps.

|  | Temperature | Processing time |
|---|---|---|
| Color developing | 33° C. | 3 min. 30 sec. |
| Bleach-fix | 33° C. | 1 min. 30 sec. |
| Washing | 33° C. | 3 min. |
| Drying | 50 to 80° C. | 2 min. |

The compositions of the processing solutions are:

| Color developer | |
|---|---|
| Benzyl alcohol | 12 ml |
| Diethylene glycol | 10 ml |
| Potassium carbonate | 25 g |
| Sodium bromide | 0.6 g |
| Sodium sulfite anhydrous | 2.0 g |
| Hydroxylamine sulfate | 2.5 g |
| N-ethyl-N-β-methanesulfonamideethyl-3-methyl-4-aminoaniline sulfate | 4.5 g |
| Water to make 1 liter | |
| Adjust pH to 11 with NaOH | |

| Bleach-fixer | |
|---|---|
| Ammonium thiosulfate | 120 g |
| Sodium metabisulfite | 15 g |
| Sodium sulfite anhydrous | 3 g |
| Ammonium-ferric ethylenediaminetetraacetate | 65 g |
| Water to make 1 liter | |
| Adjust pH to 6.7–6.8 | |

The maximum density of each of the processed Samples 1 to 12 was measured with a densitometer Kd-7R manufactured by KONICA Corporation.

A reflection spectrum of the dye image of each sample was measured with an automatic recording spectrophotometer Model 3210 manufactured by Hitachi Ltd., equipped with an integrating sphere, to determine λmax at a density of 1.0. (reference: magnesium oxide)

There was determined a wavelength ($\lambda_{0.2}$) in a shorter wavelength region, in which an absorbance is 20% of that at λmax, and a sharpness of the absorption spectrum in the shorter wavelength region was defined by the following equation:

$$\Delta \lambda s = \lambda max - \lambda_{0.2}$$

This indicates that the smaller the Δλs is, the sharper the absorption in the shorter wavelength region is.

The results are shown in Table 1.

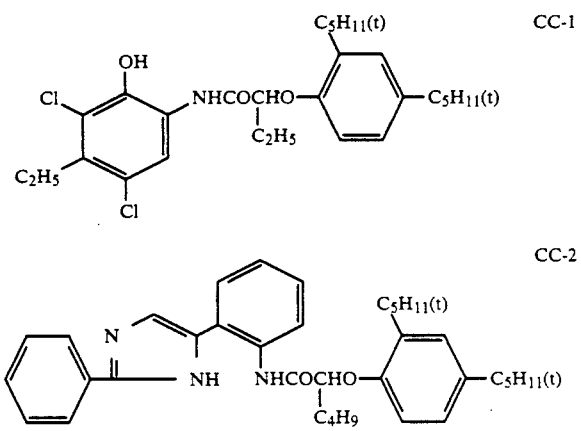

Comparative couplers:

TABLE 1

| Sample No. | Coupler | Dmax | Δλs |
|---|---|---|---|
| 1 (Comparative) | CC-1 | 2.15 | 145 |
| 2 (Comparative) | CC-2 | 2.50 | 120 |
| 3 (Invention) | 1 | 2.87 | 105 |
| 4 (Invention) | 2 | 2.76 | 112 |
| 5 (Invention) | 3 | 2.25 | 108 |
| 6 (Invention) | 6 | 2.24 | 110 |
| 7 (Invention) | 7 | 2.20 | 120 |
| 8 (Invention) | 8 | 2.40 | 112 |
| 9 (Invention) | 14 | 2.28 | 106 |
| 10 (Invention) | 15 | 2.45 | 108 |
| 11 (Invention) | 16 | 2.55 | 112 |
| 12 (Invention) | 25 | 2.47 | 108 |

To the above bleach-fixer (hereinafter referred to as 'new BF') used for processing the above samples were added 5 g of hydrosulfite to reduce a bleaching power to prepare intentionally a used bleach-fixer (hereinafter referred to as 'used BF'). The sample was processed in the used BF in the same manner as in the above.

The maximum densities of the cyan dyes were compared to calculate a color recoverability (%) according to the following equation:

Color recoverability (%) =

$$\frac{\text{Dmax when processed in used } BF}{\text{Dmax when processed in new } BF} \times 100$$

The results are shown in Table 2.

TABLE 2

| Sample No. | Color recoverability(%) |
|---|---|
| 1 (Comparative) | 65 |
| 2 (Comparative) | 68 |
| 3 (Invention) | 86 |
| 4 (Invention) | 86 |
| 5 (Invention) | 84 |
| 6 (Invention) | 82 |
| 7 (Invention) | 88 |
| 8 (Invention) | 84 |
| 9 (Invention) | 82 |
| 10 (Invention) | 85 |
| 11 (Invention) | 83 |

TABLE 2-continued

| Sample No. | Color recoverability(%) |
|---|---|
| 12 (Invention) | 85 |

As is apparent from tables 1 and 2, the cyan coupler of the invention is capable of forming a dye having a high density and a good sharpness in an absorption spectrum in a shorter wavelength region as well as an excellent color recoverability.

EXAMPLE 2

Preparation of Silver Halide Emulsion

The three different silver halide emulsions given in Table 3 were prepared by a double-jet precipitation method.

TABLE 3

| Emulsion No. | AgCl % | AgBr % | Average grain size μm | Chemical sensitizer | Spectral Sensitizing dye |
|---|---|---|---|---|---|
| Em - 1 | 99.5 | 0.5 | 0.67 | Sodium thiosulfate[*1] | SD-1[*3] |
| Em - 2 | 99.5 | 0.5 | 0.46 | Chloroauric acid[*2] | SD-2[*4] |
| Em - 3 | 99.5 | 0.5 | 0.43 | | SD-3[*5] |

[*1] 2 mg per mol of silver halide
[*2] 5 × 10⁻⁵ mol per mol of silver halide
[*3] 0.9 millimol per mol of silver halide
[*4] 0.7 millimol per mol of silver halide
[*5] 0.2 millimol per mol of silver halide After completion of the chemical sensitization, an emulsion stabilizer STB-1 was added to each of the emulsions in an amount of $5 \times 10^{-3}$ mol per mol of silver halide.

Preparation of Silver Halide Color Photographic Light-sensitive Material Samples The following layers 1 through 7 were simultaneously coated in order on a paper support whose both sides were laminated with polyethylene, whereby the light-sensitive material Samples 13 through 23 were prepared. The added amounts are per m².

Layer 1 containing 1.2 g of gelatin, 0.29 g (in silver equivalent) of a blue-sensitive silver halide emulsion (Em-1), and 0.3 g of dinonyl phthalate (DNP) dissolving 0.75 g of a yellow coupler Y-1, 0.3 g of a stabilizer ST-1 and 0.015 g of 2,5-dioctylhydroquinone HQ-1.

Layer 2 containing 0.9 g of gelatin and 0.2 g of dioctyl phthalate (DOP) dissolving 0.04 g of HQ-1.

Layer 3 containing 1.4 g of gelatin, 0.2 g of a green-sensitive silver halide emulsion (Em-2), 0.3 g of DOP dissolving 0.5 g of a magenta coupler M-1, 0.25 g of a stabilizer ST-2 and 0.01 g of HQ-1, and 6 mg of a filter dye AI-1.

Layer 4 containing 1.2 g of gelatin, 0.3 g of DNP dissolving 0.6 g of a UV absorber UV-1 and 0.05 g of HQ-1.

Layer 5 containing 1.4 g of gelatin, 0.20 g of a red-sensitive silver halide emulsion (Em-3), and 0.3 g of DOP dissolving 0.7 millimol of a cyan coupler indicated in Table 4 (CC-1: 0.9 millimole), 0.01 g of HQ-1 and 0.3 g of ST-1.

Layer 6 containing 1.1 g of gelatin, 0.2 g of DOP dissolving 0.2 g of UV-1, and 5 mg of a filter dye AI-2.

Layer 7 containing 1.0 g of gelatin and 0.05 g of sodium 2,4-dichloro-6-hydroxytriazine.

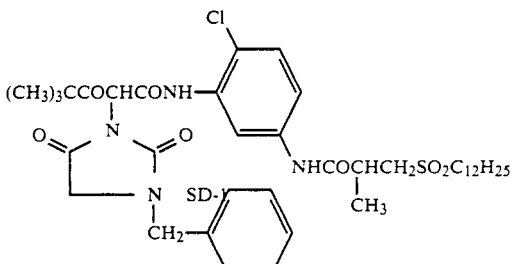

Y-1

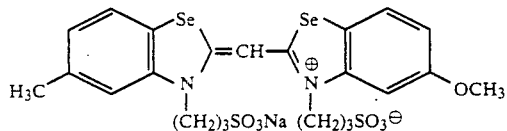

SD-1

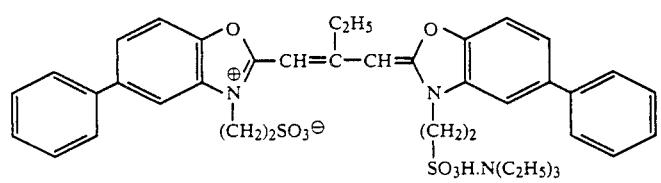

SD-2

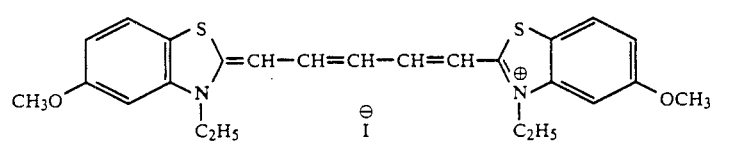

SD-3

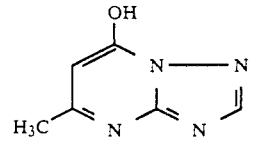

STB-1

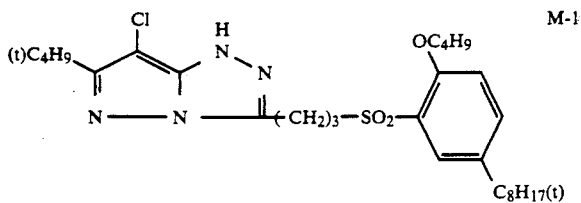
M-1

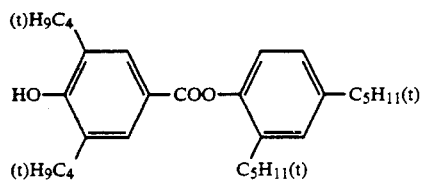
ST-1

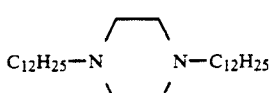
ST-2

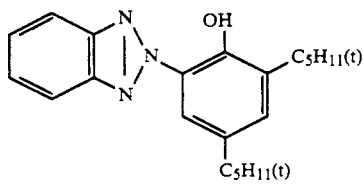
UV-1

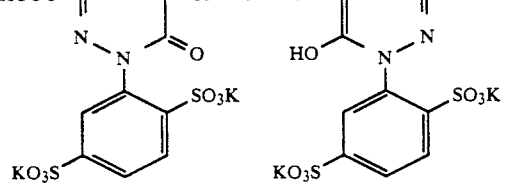
AI-1

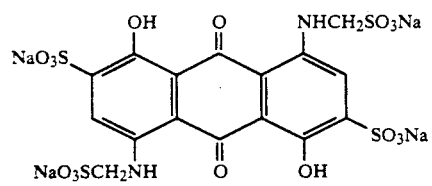
AI-2

A color checker manufactured by Macbeth Co. was photographed with KNOICA COLOR GX-100 film, and the film was processed to prepare a negative film. A negative image was printed on the above Samples 13 to 23 with a tone of a gray portion thereof adjusted, and a color reproducibility of the respective colors in each sample was evaluated. The results are shown in Table 4.

Processing Steps

| | Temperature | Processing time |
|---|---|---|
| Color developing | 34.7 ± 0.3° C. | 45 seconds |
| Bleach-fixing | 34.7 ± 0.5° C. | 45 seconds |
| stabilizing | 30 to 34° C. | 90 seconds |
| Drying | 60 to 80° C. | 60 seconds |

| Color developer | |
|---|---|
| Pure water | 800 ml |
| Triethanolamine | 8 g |
| N,N-diethylhydroxylamine | 5 g |
| Potassium chloride | 2 g |
| N-ethyl-N-β-methanesulfonamideethyl-3-methyl-4-aminoaniline sulfate | 5 g |
| Sodium tetrapolyphosphate | 2 g |
| Potassium carbonate | 30 g |
| Potassium sulfite | 0.2 g |
| Brightening agent, 4,4'-diaminostilbene-disulfonic acid derivative | 1 g |
| Pure water to make 1 liter | |
| Adjust pH to 10.2 | |

| Bleach-fixer | |
|---|---|
| Ammonium-ferric ethylenediaminetetraacetate dihydrate | 60 g |
| Ethylenediaminetetraacetic acid | 3 g |
| Ammonium thiosulfate (70% solution) | 100 ml |
| Ammonium sulfite (40% solution) | 27.5 ml |
| Water to make 1 liter | |
| Adjust pH to 5.7 with potassium carbonate or glacial acetic acid | |

| Stabilizer | |
|---|---|
| 5-Chloro-2-methyl-4-isothiazoline-3-one | 1 g |
| 1-Hydroxyethylidene-1,1-diphosphonic acid | 2 g |
| Water to make 1 liter | |
| Adjust pH to 7.0 with sulfuric acid or potassium hydroxide | |

TABLE 4

| | | | Color reproducibility* | | |
|---|---|---|---|---|---|
| Sample No. | Coupler | Green | Red | Magenta | Cyan |
| 13 (Comparative) | CC-1 | C | B | B | B |
| 14 (Invention) | 1 | A | A | A | A |
| 15 (Invention) | 3 | A | A | A | A |
| 16 (Invention) | 5 | A | A | A | A |
| 17 (Invention) | 9 | A | A | A | A |
| 18 (Invention) | 13 | A | A | A | A |
| 19 (Invention) | 17 | A | A | A | A |
| 20 (Invention) | 20 | A | A | A | A |
| 21 (Invention) | 22 | A | A | A | A |
| 22 (Invention) | 23 | A | A | A | A |
| 23 (Invention) | 25 | A | A | A | A |

*A: Excellent in hue and chroma
B: Slightly bad in hue and chroma
C: Bad in hue and chroma

EXAMPLE 3

Samples 24 to 31 were prepared in the same manner as in Example 2 except that the cyan coupler in Layer 5 was replaced as shown in Table 5.

Each sample was exposed through an optical wedge, processed in the same manner as in Example 2, and then subjected to an accelerated aging test wherein the processed sample was exposed to a xenon light for 100 hours under an atmospheric condition of 30° C./20%RH, to measure a residual rate of a cyan dye image having a density of 1.0. The results are shown in Table 5.

CC-3

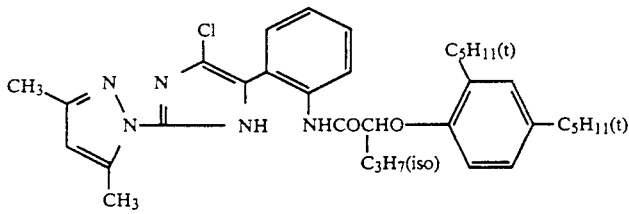

TABLE 5

| Sample No. | Coupler | Dye residual rate (%) |
|---|---|---|
| 24 (Comparative) | CC-2 | 42 |
| 25 (Comparative) | CC-3 | 35 |
| 26 (Invention) | 2 | 80 |
| 27 (Invention) | 5 | 88 |
| 28 (Invention) | 9 | 78 |
| 29 (Invention) | 10 | 85 |
| 30 (Invention) | 15 | 88 |
| 31 (Invention) | 20 | 80 |

As is apparent from the results in Table 5, the coupler of the invention has a much higher dye residual rate than the conventional imidazole cyan coupler, which means that the light fastness thereof is remarkably improved.

What is claimed is:

1. A silver halide photographic light-sensitive material comprising a support and provided thereon photographic component layers including at least one silver halide light-sensitive emulsion layer containing silver halide grains and a cyan coupler represented by the following Formula I;

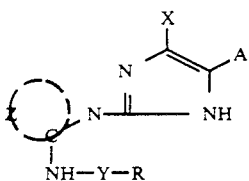

wherein A represents an organic group; X represents a hydrogen atom or a group capable of splitting off upon a reaction with an oxidation product of a color developing agent; Z represents a group of atoms capable of forming a five or six-membered heterocyclic ring together with carbon and nitrogen atoms; Y represents a divalent linkage group or a bond; and R represents a hydrogen atom or an organic group.

2. The light-sensitive material of claim 1, wherein A is an alkyl group, an aryl group, a heterocyclic group, —NHCOR', —NHSO₂R', —NHCONHR', —NHCOOR', or —Y'R", in which R' represents a hydrogen atom, an alkyl group or an aryl group; R" represents an alkyl group, an aryl group or a heterocyclic group; and Y' represents an oxygen, nitrogen or sulfur atom.

3. The light-sensitive material of claim 2, wherein A is an aryl group or a heterocyclic group.

4. The light-sensitive material of claim 2, wherein A is an aryl group having in an ortho-position a group capable of forming a hydrogen bond.

5. The light-sensitive material of claim 4, wherein the group capable of forming a hydrogen bond is an amide group, a sulfonamide group, a carbamoyl group or a sulfamoyl group.

6. The light-sensitive material of claim 1, wherein the group represented by X and capable of splitting off upon a reaction with an oxidation product of a developing agent is a halogen atom, a hydroxyl group, an alkoxy group, an aryloxy group, a heterocyclicoxy group, an acyloxy group, a sulfonyloxy group, an alkoxycarbonyloxy group, an aryloxycarbonyl group, an alkyloxalyloxy group, an alkoxyoxalyloxy group, an alkylthio group, a mercapto group, an arylthio group, a heterocyclicthio group, an alkoxythiocarbonylthio group, an acylamino group, a substituted amino group, a nitrogen-containing heterocyclic group having a bonding site on nitrogen, a sulfonamide group, an alkyloxycarbonylamino group, an aryloxycarbonylamino group, or a carboxyl group.

7. The light-sensitive material of claim 1, wherein the heterocyclic group formed by Z together with the carbon and nitrogen atoms is a pyrrolyl group, an imidazolyl group, a pyrazolyl group, a pyrrolidinyl group, an imidazodinyl group, a pyrazolidinyl group, a piperazinyl group, a morpholinyl group, or a thiazolidinyl group, each of which may have a substituent other than —NH—Y—R in addition to the —NH—Y—R group.

8. The light-sensitive material of claim 1, wherein Y is the divalent linkage group.

9. The light-sensitive material of claim 8, wherein the divalent linkage group is —CO—, —COO—, —SO₂— or —CONH—.

10. The light-sensitive material of claim 1, wherein the organic group represented by R is an alkyl group, an aryl group or a heterocyclic group.

11. The light-sensitive material of claim 1, wherein a content of the cyan coupler is $2 \times 10^{-3}$ to $8 \times 10^{-1}$ mol per mol of silver halide.

12. The light-sensitive material of claim 11, wherein the content is $1 \times 10^{-2}$ to $5 \times 10^{-1}$ mol per mol of silver halide.

13. The light-sensitive material of claim 1, wherein Y is the bond.

14. The light-sensitive material of claim 11, wherein
A is an alkyl group, an aryl group, a heterocyclic group, —NHCOR', —NHSO₂R', —NHCONHR', —NHCOOR', or —Y'R", in which R' represents a hydrogen atom, an alkyl group or an aryl group; R" represents an alkyl group, an aryl group or a heterocyclic group; and Y' represents an oxygen, nitrogen or sulfur atom;

the group represented by X and capable of splitting off upon a reaction with an oxidation product of a developing agent is a halogen atom, a hydroxyl. group, an alkoxy group, an aryloxy group, a heterocyclicoxy group an acyloxy group, a sulfonyloxy group, an alkoxycarbonyloxy group, an aryloxycarbonyl group, an alkyloxalyloxy group, an alkoxyoxalyloxy group, an alkylthio group, a mercapto group, an arylthio group, a heterocyclicthio group, an alkoxythiocarbonylthio group, an acylamino group, a substituted amino group, a nitrogen-containing heterocyclic group having a bonding site on nitrogen a sulfonamide group, an alkyloxycarbonylamino group, an aryloxycarbonylamino group, or a carboxyl group;

the heterocyclic group formed by Z together with the carbon and nitrogen atoms is a pyrrolyl group, an imidazolyl group, a pyrazolyl group, a pyrrolidinyl group, an imidazodinyl group, a pyrazolidinyl group, a piperazinyl group, a morpholinyl group, or a thiazolidinyl group each of which may have a substituent other than —NH—Y—R in addition to the —NH—Y—R group;

Y is a bond or a divalent linkage group; and the organic group represented by R is an alkyl group, an aryl group or a heterocyclic group.

15. The light-sensitive material of claim 14, wherein the content is $1 \times 10^{-2}$ to $5 \times 10^{-1}$ mol per mol of silver halide.

16. The light-sensitive material of claim 14, wherein Y is the divalent linkage group and is —CO—, —COO—, —SO$_2$— or —CONH—.

17. The light-sensitive material of claim 14, wherein A is an aryl group or a heterocyclic group.

18. The light-sensitive material of claim 17, wherein A is an aryl group having in an ortho-position a group capable of forming a hydrogen bond selected from the group consisting of an amide group, a sulfonamide group, a carbamoyl group and a sulfamoyl group.

19. A silver halide photographic light-sensitive material, comprising a support and provided thereon photographic component layers including at least one silver halide light-sensitive emulsion layer containing silver halide grains and a cyan coupler and wherein the cyan coupler is represented by the following formula and the following definitions:

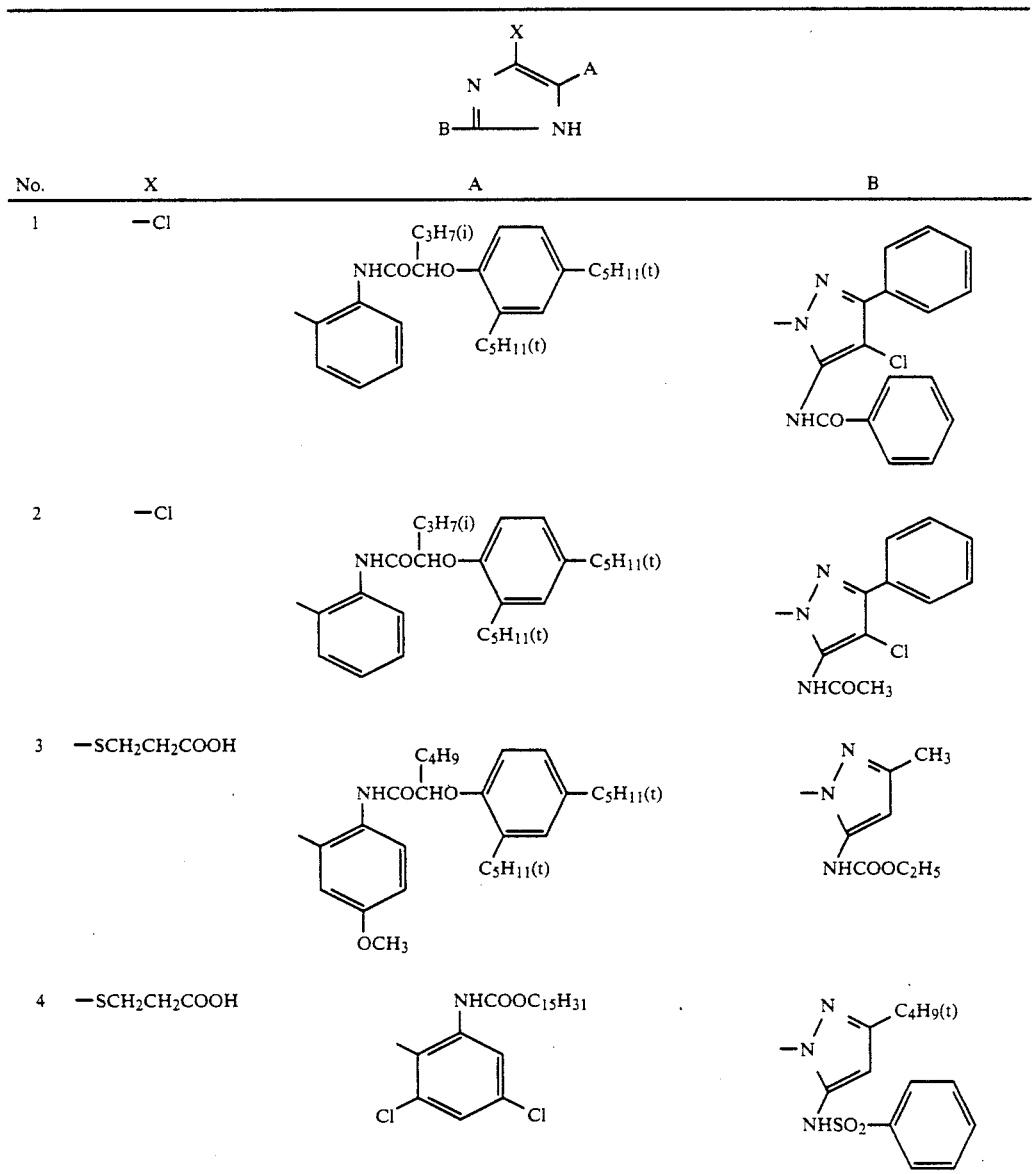

-continued $$\begin{array}{c} X \\ | \\ N=\overset{}{\underset{}{C}}-A \\ || \\ B-C=NH \end{array}$$

| No. | X | A | B |
|---|---|---|---|
| 5 | —Cl | 2-methylphenyl-NHCOCH(C₃H₇(i))O-(2,4-di-C₅H₁₁(t))phenyl | 1-methyl-3-C₄H₉(t)-5-[NHCO-(2,3,4,5,6-pentafluorophenyl)]pyrazole |
| 6 | —Cl | 2-methylphenyl-NHSO₂-(2-OC₈H₁₇, 5-C₈H₁₇(t))phenyl | 1-methyl-2-(NHCOC₃H₇)pyrrolidine |
| 7 | —Cl | (2-methyl-4-chlorophenyl)-NHSO₂-(4-OC₁₂H₂₅)phenyl | 1-(4,5-dichloro)-2-(NHCOOCH₃)imidazole |
| 8 | —Cl | (2-methyl-4-NHCOC₆H₅-phenyl)-NHCOCH(C₆H₁₃)O-(2,4-di-C₄H₉(t))phenyl | 3-[NHSO₂N(CH₃)₂]morpholine |
| 9 | —Cl | 2-methylphenyl-NHCOOC₂H₅ | 1-methyl-3-phenyl-4-chloro-5-[NHCOCH(C₃H₇(i))O-(2,4-di-C₅H₁₁(t))phenyl]pyrazole |
| 10 | —Cl | 2-methylphenyl-NHCOOC₁₂H₂₅ | 1-methyl-3-(NHC₆H₅)-4-CH₃-5-(NHCOCF₃)pyrazole |

-continued

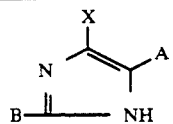

| No. | X | A | B |
|---|---|---|---|
| 11 | —Cl | —C_8H_17(t) | (pyrazole with CH_3, phenyl, NHCONH-phenyl substituents) |
| 12 | —H | (NHCOCH(C_3H_7(i))- linked to 2,4-di-C_5H_11(t) phenoxy, with o-tolyl) | (pyrazole with C_4H_9(t) and NH_2) |
| 13 | —Cl | (o-tolyl-NHCO(CH_2)_2OCOCH_2-O-phenyl with Cl and C_8H_17) | (piperazine with three NHCOCH_3 / N—COCH_3 groups) |
| 14 | —Cl | (2,4-dichlorophenyl) | (pyrazole with COOC_2H_5, NHCOCH(C_12H_25)O-phenyl-C_4H_9(t)-OH) |
| 15 | —O-phenyl | (NHCO-pentafluorophenyl with 2,4-dimethylphenyl) | (pyrazole with C_4H_9(t), OC_8H_17, NHSO_2-phenyl-C_8H_17(t)) |
| 16 | —S-(2-OCH_3, 5-C_4H_9(t))phenyl | (o-tolyl-NHCOCH(C_12H_25)O-2-chlorophenyl) | (pyrazole with thienyl and NHCOCF_3) |
| 17 | —Cl | (o-tolyl-NHCOCH(C_12H_25)O-phenyl with OH and C_4H_9(t)) | (pyrazole with OC_2H_5, Cl, NHCO-2,4,6-trichlorophenyl) |

-continued

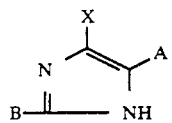

| No. | X | A | B |
|---|---|---|---|
| 18 | —Cl | (2-methyl-3-methoxyphenyl)NHCOCH(C4H9)O-(2,4-di-t-C4H9-phenyl) | 1-methyl-3-(COOC3H7)-5-[NHSO2-(4-N(CH3)2-phenyl)]pyrazole |
| 19 | —Cl | 4-hydroxy-3-methyl-phenyl-NHSO2-(2-C16H33-phenyl) | 1-methyl-3-CH3-4-NO2-5-NHCOCH3-pyrazole |
| 20 | —Cl | (2-methylphenyl)NHCOCH(C3H7(i))O-(2,4-di-t-C5H11-phenyl) | 1-methyl-3-C4H9(t)-5-[NHCO-(pentafluorophenyl)]pyrazole |
| 21 | —Cl | (2-methylphenyl)NHCOCH(C3H7(i))O-(2,4-di-t-C5H11-phenyl) | 1-methyl-3-C4H9(t)-5-NHCOCF3-pyrazole |
| 22 | —Cl | 4-CF3-3-CH3-phenyl-NHCOOC12H25 | 1-methyl-3-C4H9(t)-5-[NHCO-(4-CH3-phenyl)]pyrazole |
| 23 | —Cl | (2-methyl-thiophen-3-yl)NHCOCH(C3H7(i))O-(2,4-di-t-C5H11-phenyl) | 1-methyl-3-C4H9(sec)-4-Cl-5-NHCOOC8H17-pyrazole |
| 24 | —Cl | 1-methyl-2-methyl-pyrrole | 1-methyl-3-C15H31-5-(NHCO-phenyl)pyrazole |

-continued
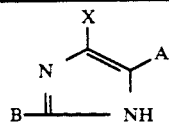
| No. | X | A | B |
|---|---|---|---|
| 25 | —Cl | —NHCOCH(C₆H₁₃)O—[3,5-di-C₅H₁₁(t)-phenyl] | 3-ethyl-5-(NHCOC₂F₅)-pyrazol-1-yl |